United States Patent [19]
Gurr et al.

[11] Patent Number: 5,824,876
[45] Date of Patent: *Oct. 20, 1998

[54] PLANT PARASITIC NEMATODE CONTROL

[75] Inventors: Sarah Jane Gurr, Oxford; Michael John McPherson, Dewsbury; Howard John Atkinson, Leeds; Dianna Joy Bowles, North Yorkshire, all of England

[73] Assignee: Advanced Technologies (Cambridge) Limited, Cambridge, England

[ * ] Notice: The term of this patent shall not extend beyond the expiration date of Pat. No. 5,589,622.

[21] Appl. No.: 727,770

[22] Filed: Oct. 8, 1996

Related U.S. Application Data

[63] Continuation of Ser. No. 356,790, Dec. 13, 1994, Pat. No. 5,589,622, which is a continuation of Ser. No. 988,954, Jun. 28, 1993, abandoned.

[51] Int. Cl.$^6$ .......................... C12N 15/29; C12N 15/82; C12N 15/09; A01H 5/00
[52] U.S. Cl. .................... 800/205; 800/DIG. 42; 800/DIG. 40; 800/DIG. 44; 800/DIG. 26; 435/172.3; 435/320.1; 435/419; 435/418; 435/6; 435/199; 435/219; 536/23.6; 536/24.1; 536/24.5
[58] Field of Search ........................... 800/205, DIG. 40, 800/DIG. 42, DIG. 44, DIG. 26; 435/172.3, 320.1, 419, 418, 6, 199, 219; 536/23.6, 24.1, 24.5

[56] References Cited

U.S. PATENT DOCUMENTS 5,589,622 12/1996 Gurr et al. ............................... 800/205

*Primary Examiner*—David T. Fox
*Assistant Examiner*—Thomas Haas
*Attorney, Agent, or Firm*—Morgan & Finnegan, LLP

[57] ABSTRACT

A method of controlling nematodes, the method includes the steps of identification of a gene induced within a successfully infected plant by nematode infection of said plant and modifying the gene to confer nematode resistance to the plant.

16 Claims, No Drawings

PLANT PARASITIC NEMATODE CONTROL

This application is a continuation of Ser. No. 08/356,790, filed on Dec. 13, 1994, now U.S. Pat. No. 5,589,622, which is a continuation of application Ser. No. 07/988,954, filed on Jun. 28, 1993, now abandoned.

BACKGROUND OF THE INVENTION

This invention relates to control of plant parasitic nematodes, especially to a method of control of root cyst nematodes. This invention also relates to the introduction of nematode resistance into plants of a wide number of species which are susceptible to root cyst nematodes, for example potato plants (*Solanum tuberosum*)

Cyst nematodes (principally Heterodera and Globodera spp) are key pests of major crops. They are responsible for direct loss in yield and also for indirect losses for instance due to the cost of pesticide and non-optimal use of land or rotation. Potato cyst nematodes (*Globodera rostochiensis* and *Globodera pallida*) are key pests of the potato in UK, many other parts of Europe and in other principal potato growing areas. *Heterodera glycines* (Soybean cyst nematode) has an economic effect on soybean that may exceed S500m/y in USA alone. *Heterodera schachtii* (beet cyst nematode) is a major problem for sugar beet growers in Europe and USA. *Heterodera avenae* (cereal cyst nematode) has a worldwide economic status.

Economically significant densities of cyst nematodes usually cause stunting of crop plants. The root system is smaller than for uninfected plants, resulting in leaves showing symptoms of mineral deficiencies with an increased risk of wilting in dry soil conditions. Yield losses are related to the density of cyst nematode present at planting and in severe cases may be substantially above 50% for crops such as potato and soybean.

Current control depends upon chemicals, cultural techniques and resistant varieties all of which may be used in an integrated manner. Improved control in required. Nematicides are among the most unacceptable crop protection chemicals in widespread use. For instance Aldicarb and its breakdown products are highly toxic to mammals and have polluted groundwater. The result is that governments of several states within USA have placed restriction on the use of this nematicide. In The Netherlands there is a policy of reduction in nematicide use over a five year period. Cultural control is not an ideal solution to nematode control because measures such as crop rotation include hidden losses that are unacceptable to specialist growers or those with few economic alternative crops.

Resistance of a plant to nematodes may be effected by the inability of the nematode to reproduce on a genotype of a host plant species, and dominant partially dominant and recessive modes of inheritance occur based on one to several plant genes. However, their commercial value is limited for the plant breeder and farmer. For instance, it has been observed in Europe that in potato different sources of resistance occur and create subdivisions of the nematode populations in Europe, as in the case of the single dominant gene H1 which confers resistance against *G. rostochiensis* (Ro1 and Ro4) but not other forms of this species (Ro2, Ro3 and Ro5).

The cultivar Maris Piper expresses H1 and is widely used In the UK against *G. rostochiensis* but its use has been correlated with an increased prevelance of *G. pallida* which is able to reproduce in the presence of H1. The problem posed by resistance-breaking pathotypes occurs for other cyst nematodes and sources of resistance. In some cases, sources of resistance are polygenic, presenting more difficulties for the plant breeder. In addition the resistance in some cultivars in quantitative rather than qualitative in nature and so increased nematode multiplication may occur with time in response to frequent use of such cultivars.

The interface between plant and pathogen is a site of key importance in the determination of susceptibility or resistance to invasion. During early determinative stages of the invasion process, the interface is restricted to a very small number of plant cells at the local site of infection. Later redifferentiation of existing plant cells forms a syncytium from which the animal feeds. The syncytium is induced by second-stage juveniles after they have migrated into the roots of a host probably in response to secretion very small number of plant cells at the local site of infection. Later redifferentiation of existing plant cells forms a syncytium from which the animal feeds. The syncytium is induced by second-stage juveniles after they have migrated into the roots of a host probably in response to secretions released by the animal into an initial feeding cell. When the plant is susceptible, the syncytium increases in volume and is maintained throughout the feeding period of the nematode. In the case of females this may occupy several weeks. The cell biology of the syncytium is well characterized.

This invention seeks to provide a method of conferring nematode resistance in a plant which can be universal in its protection against cyst nematodes and can have long term persistence. The Invention contrasts with any method which may involve the use of a known resistance gene being instead based on the use of genes which are specifically part of the susceptibility to nematode attack.

It relates to identification of previously unknown genes expressed specifically within the feeding site of a cyst nematode and subsequent to the attachment by the nematode. Identification of the genes may be achieved through use of a polymerase chain reaction (PCR). Previously the limited cellular interface between plant and pathogen has limited understanding of the molecular biology at the interface. The invention further relates to novel use of such genes to direct, upon attack, the release of materials specifically within the feeding site, which are toxic to either plant cell or nematodes. The specific release of such materials enables compounds to be used, which if expressed constitutively within the plant, would impair plant growth or result in an unacceptable toxicological hazard. A range of such compounds is already known and standard biotechnological techniques are available for their application with the invention.

Corresponding nematode specific genes can be tobacco.

Syncytium development is also known to be similar for a variety of cyst nematodes. Use of a specifically triggered gene has therefore universal applicability to all cyst nematodes. The includes, but is not limited to: *Globodera pallida* and *Globodera rostochiensis* (potato cyst nematodes). *Heterodera glycines* (soybean cyst nematodes). *Heterodera shachtii* (beat cyst nematode). *Heterodera avenae* (cereal cyst nematode). *Heterodera cryzae* (rice cyst nematode) and *Globodera tabacum* (tobacco cyst nematode).

In this specification the term "gene" refers to a DNA sequence that incorporates (1) upstream (5') regulatory signals Including the promoter. (2) a coding region specifying the product, protein or RNA of the gene, (3) downstream (3') regions including transcription termination and polyadenylation signals (4) associated sequences rquired for efficient and specific expression.

The term "promoter" refers to a region of a DNA sequence that incorporates the necessary signals for the efficient expression of a coding sequence. This may include sequences to which an RNA polymerase binds but is not limited to such sequences and may include regions to which other regulatory proteins bind, together with regions involved in the control of protein translation and may include coding sequence.

SUMMARY OF THE INVENTION

According to the first aspect of the present invention there is provided a method of controlling nematodes, the method including the steps of identification of a gene induced within a successfully infected plant by nematode infection of said plant and modifying the gene to confer nematode resistance to the plant.

The methods preferred comprise Identification of genes induced at the feeding site by nematode infection of a plant, said genes being characteristic of nematode infection.

A preferred method of identification of the genes includes the steps of:

constructing a cDNA library by use of a polymerase chain reaction (PCR);

comparing said library with cDNA of infected and uninfected plants; and identifying a cDNA clone representing a gene expressed at the feeding site and using the cDNA clone to isolate a corresponding genomic clone.

The gene or part thereof may include a DNA sequence consisting essentially of the sequence selected from the group comprising:

GCCCAAACTTTCCGGTGTACTCCTTGTC-CTTGTTTTTCTAGTCTTTTACCTATCCAAC AAAAATTTCTCGCCAAAAAAGGGT-TATAACACCGCGATAAAGCTCTTAAATAATG (formula 1)

AACATCGGCTCCAAGAGAGGAAAAG-GCACGAAGAATGGACAATTTTACCAAAAGCATTT CCTTAGGCTCATAAAGCATTTTAAAC-CCCGATGCTGTTGTTGTTTGAAGG (formula 2)

GTATCCACGCCTCTGAATAGCACAGAAA-CAGATCTACAAGAAAACCACACATATTTTTG CAGTTGGAGAAATAACGAGCCATTG-TAATTGNCGGTTCTAAGNNTCAAGC-GATCAAAAT TAAATTAAAGTTACCAACGG (formula 3)

CATGACGATCGACAAAATCATTGAG-GAACTGGATAACACCGNNCGGCTGC-CGGGGCTGGC GAATCTGTGGGTNCCGCCAAT-TCGTAACCGTATCGATATGCTCTCAACCGGCATTAAAA (formula 4)

CACCATTACACTGGCCCAGGTGCAGTA-CAGCATCTGGGTGACGNGGAAANANNUCCTGGT ACTTTTCGGAACTATGCACACCGGCTGC-TATCAAAGCCTGAAGGCCTGCATA (formula 5)

GTCGCTACCTTTCGGGACGCAATACCG-TATTGCTGCGCTTCCAGAGAGTCACCTACCGCT TTGAATGAC (formula 6)

GCGCCGCCGCACATCGCGGGCTCGGNG-GCTACGGCTACGOAGGTTGCACAACTTGCGGAC GCAAATAAACGCCCAACAATCGG (formula 7)

CGTGAGTCAGTNAtTCGTATTACAAT-TCACTGGCCCTCOTTTTACAACGTCCTCGTCACT GGCAAACCC (formula 8)

wherein
A is adenine
C is cytosine
T is thymine
G is guanine
and N is an unassigned nucleotide The DNA sequence mentioned above or in the following statements of invention may consist essentially or any of the above sequences (formulae 1 to 8) or equivalent nucleotide sequences representing allels or polymorphic variants of these genes.

According to the second aspect of the present invention a nematode resistant plant incorporates a gene or part thereof, the gene including a DNA sequence consisting essentially of a sequence selected from the group comprising:

GCCCAAACTTTCCGTTGTACTCCTTCTC-CTTGTTTTTTGTAGTCTTTTACCTATCCAAC AAAAATTTCTCGCCAAAAAAGCGT-TATAACACCCCGATAAACCTCTTAAATAATG (formula 1)

AACATCGGGTCCAAGAGAGCAAAACG-CACCAAGAATGGACAATTTTACCAAAACCATTT CCTTAGCCTCATAAAGCATTTTAAAC-CCCCATGCTGTTGTTGTTTGAAGG (formula 2)

GTATCCACGCCTCTGAATAGCACAGAAA-CAGAGTCTACAAGAAAACCACACATATTTTTG CAGTTGGAGAAATAACGAGCCATTG-TAATTGUCOGTTCTAAGNNTCGAAGC-GATCAAAAT TAAATTAAAGTTAGCAACGG (formula 3)

CATCACGATGGACAAAATCATTGAC-GAACTGGATAACACCCNNCGGCTGC-CGGGCTGCC GAATCTGTGGGTNCCGCCAATTCG-TAACCGTATCGATATGCTCTCAACCGCCATTAAAA (formula 4)

CAGCATTACACTGGCCCAGGTGCAGTA-CAGCATCTCCGTGACGNGCAAANANNNCCTCGT ACTTTTCGGAACTATGCACACCGGCTGC-TATCAAAGCCTCAACCCCTCCATA (formula 5)

GTCCCTACCTTTACGCACGCAATAC-CCTATTGCTCCGCTTCCAGACACTCAC-CTACCGCT TTGAATGAC (formula 6)

GCCCCGCGGCACATCGGGGCCTC-CCNCGCTACGGCTACGGACGTTGCA-CAACTTGCCGAC GCAAATAAACCCCCAA-CAATCGG (formula 7)

CGTGAGTCAGTMACTCGTATTACAAT-TCACTGGCCGTCGTTTTACAACGTCOTCGTGACT GGGAAACCC (formula 8)

wherein
A is adenine
C is cytosine
T is thymine
G is guanine
and N is an unassigned nucleotide According to the third aspect of the present invention there is provided use of a plant gene promoter region identified by the method of a preceding aspect of this invention for conferring root cyst nematode resistance to a plant The method may comprise the steps of modifying or transforming the plant with the promoters to genes of preceding aspect of this invention and further modifying the plant by linkage to a means of killing a plant cell that attempts re-differentiation towards syncytial development following stimulation by a nematode.

The promoter sequence of a gene clone which is expressed within the feeding site could be used to promote the following substances:

a. A toxic protein, peptide or an enzyme such as DNAse, RNAse or a proteinase b. A multigene toxic syndrome, whereby, for example, the promoter may express a protein or peptide which is inactive until activated by a protein produced by a gene coupled to another promoter sequence identified as feeding site specific. The product of a first gene A may be inactive until attacked by the product of the second gene B to form a new A' which represents an active toxin or protease. Alternatively A may be inactive without B such that only A-B molecules are active.

c. Antisense RNA, including one or more antisense RNA genes being the same as the gene sequences of the invention or other feeding site specific genes. That is the promoter may be used to direct the production of its own antisense RNA. This dramatically reduces the level of the normal product. Alternatively the promoter may be used to direct expression of an antisense RNA for general cellular genes, such as an ATP synthetase, essential for cell viability.

Cyst nematode resistance may also be conferred on a plant specifically at the site of feeding, the method comprising the steps of modifying or transforming a plant with the promoters to genes of a preceding aspect of this invention in conjuction with a gene whose product has a direct lethal or pronounced sub-lethal effect on the nematode after ingestion (i.e. an anti-nematode gone product). Examples of potentially useful genes that could be used in conjunction with the current invention are:

a. a protein toxin of *Bacillus thuringiensis* (or a similar organism) having anti-nematode activity.

b. the gene for a nematode toxic protein in accordance with UK patent application number 9104617.7 (which corresponds to U.S. patent application Ser. No. 08/108,623, now U.S. Pat. No. 5,494,813.

c. an antibody that disrupts feeding by interacting with the ingestion or digestion of food such as one of the antibodies described for soybean cyst nematode including that against the dorsal pharyngeal gland (Atkinson et al, 1988 *Annal of Applied Biology* 112, 459–469) using the procedures for transgenic expression of antibodies in plants described by Hiatt, A. Cafferkey, R C. & Bowdish, K. (1989 Production of Antibodies in Transgenic Plants *Nature* 342, 76–78).

d. a protein or peptide such as a neuropeptide that would have a toxic effect upon the feeding cyst nematode following ingestion.

It will be appreciated that the level of resistance need not be absolute but it will generally be conferred to a degree which is agriculturally or economically signifcant for that plant.

The invention affords a means of providing nematode resistance that is localised to the mite of feeding or adjacent thereto of the nematode. It overcomes the need for the plant to produce constitutively an anti-nematode gene product (such an examples listed in the third aspect of the invention). This limits any detrimental effect on the plant that may arise from constitutive expression. Many crops are protectable from cyst nematodes by this invention and are therefore candidates for being genetically manipulated to express the promoters of the syncytium-characteristic genes linked to sequences that either disrupts the redifferentiation of plant cells to form a syncytium or expresses an anti-nematode gene product within the syncytium. These include the crops attack by cyst nematodes such as *Globodera pallida* and *Globodera rostochiensis* (potato cyst nematodes). *Heterodera glycines* (soybean cyst nematode), *Heterodera shachtii* (beet cyst nematode), *Heterodera avenae* (cereal cyst nematode), *Heterodera carotae* (carrot cyst nematode), *Heterodera oryzae* (rice cyst nematode) and *Globodera tabacum* (tobacco cyst nematode). A few illustrative but non-limiting examples of crops which may be protected by this invention from cyst nematodes include potato, tomato, soybean, sugar beet, oilseed rape, wheat, oats, barley, rice, carrot, brassicas and tobacco.

The invention is further described by means of example but not in any limitative sense.

The first example describes the methods used to identify, characterise and manipulate potato genes to generate resistant transgenic potato plants.

DETAILED DESCRIPTION OF THE INVENTION

EXAMPLE 1

This example illustrates the use of a susceptible cultivar of potato to *Globodera rostochiensis* pathotype Ro2 to allow identification of genes expressed within the feeding site of the nematode. Sections 1 to 5 provide details for the production of infected root tissue. The minute amounts of locally infected tissue provided quantities of RNA (Section 6) best suited to construction of a cDNA library by a PCR amplification approach (Section 7.1 to 7.4). Isolation of feeding call specific cDNA, clones was achieved by differential hybridisation screening with cDNA probes from infected and non-infected tissue (Section 7.5). Positive cDNA clones were analysed by DNA sequencing (Section 10) and the inserts used as probes in subsequent steps. An examination of temporal and spatial expression of genes was performed by Northern analysis (Section 8) using a range of plant tisues and time-course of infection. Further localisation of gene expression was achieved by in situ hybridization studies (Section 12). Genomic clones corresponding to feeding cell specific cDNA clones were isolated from a genomic DNA library (Section 11). Promoters were Identified by DNA sequence analysis (Section 11) for the development of constructs suitable for generating transgenic potato plants expressing nematode resistance (Section 13) locally within the feeding site.

1. Plant Materials

*Solanum tuberosum* cultivar Maris Piper (Scottish seed potatoes, class A) were chitted up for 24 days (Hammond-Kosack K E. Atkinson H J. Bowles D J 1990 *Changes in abundance of translatable mRNA species in potato roots and leaves following root invasion by cyst-nematode G. rostochiensis pathotypes* Physiol Mol Plant Pathol). Individual spouts were excised from growth in pouches or whole tubers were used for pot grown material.

2. Nematodes

Population of *Globodera rostochiensis* pathotype Ro1 and Ro2 cysts were maintained an dry stocks at 4° C. The cysts were soaked in tap water for 7 days at 4° C. Potato root diffusate was added (Shepherd A H 1986 In: Southey J F (ed) *Laboratory methods for work with plant and soil nematodes:* MAFF reference book 402. 6th edn) and hatching occurred after 4–7 days at room temperature.

3. Infection

Pouch material; Individual sprouts were supported in ready-made pouches (Northrup-King, Minn.). 1 cm×0.5 cm strips of Whatman GFA paper were placed under individual root tips. 50 worms in 10 ul of root diffusate wore pipetted onto each root tip which were then overlaid with a second strip of GFA. The GFA filter paper was removed 24 hours after inoculation to synchronize infections. The base was excised and pouches were irrigated in tap water.

Pot material; chitted tubers were planted in 25 cm pots in soil plus sufficient number of unhatched cysts to give a population of 50 eggs per gram soil.

Sham-inoculated pouches and pots were set up under identical conditions but without cysts.

4. Growth conditions

The infected potatoes were grown under a regime of 18 hours light at 22° C. and 6 hours dark at 18° C.

5. Harvesting and dissection

Pouch grown tissue was harvested at 4, 7, 15, and 24 days post invasion. The discolored locally infected roots were dissected directly into foil envelopes in liquid nitrogen. Root tissue directly adjacent the infected area was also dissected and frozen separately.

Pot grown tissue was harvested 26 days post Ro2 invasion. The emerging females and cysts were removed with a fine paint brush and locally infected tissue was dissected directly into liquid nitrogen in individual foil packets.

6. Isolation of total RNA

Foil packets were gently crushed with a pestle to give a powder of tissue that was stored at −70° C. until required. Powdered tissue (12 mg) was transferred to pre-cooled 20 ml disposable plastic Sarstedt tubes in liquid nitrogen before addition of 0.5 ml phenol/$CH_3Cl$/isoamyl alcohol (25:24:1) and 0.5 ml GuHCl buffer (8M Guanidinium-HCl, 20 mM HES (4-morpholino-ethanol-sulphonic acid), 20 mM $Na_2EDTA$, adjusted to pH7 with NaOH and 2-mercaptoethanol added to 50 nM. immediately prior to use). Once the tubes had thawed on ice the tissue wax homogenized by 15 strokes of a Polytron blender (Kinematica, Switzerland). The aqueous phase was re-extracted three more times with phenol before overnight precipitation at −20° C. following the addition of 0.2 vol 1M acetic acid and 0.7 vol cold 96% ethanol. RNA recovered by centrifugation at approximately 13,000 xg for 15 minutes in a microcentrifuge was washed in 400 ul 3M sodium acetate (pH 5.5) at 4° C. then in 70% cold ethanol before being finally dissolved in 30–50 ul DEPC-treated $H_2O$ and stored at −70° C.

7. Construction of a PCR-based cDNA library 7.1 cDNA synthesis 1 microgram total RNA from potato roots collected 26 days post infection with G. rostochiensis pathotype Ro2 was denatured for 5 minutes in a 70° C. water bath then rapidly cooled on ice. The sample was added to a reaction mix consisting of 4 ul 5× AMVRT buffer (250 mM Trio-HCl, pH 8.3, 250 mM KCl, 50 mM $MgCl_2$, 5 mM DDT, 5 mM EDTA, 50 ug/ml bovine serum albumini, 2 ul Oligo, $(dT_{17})$ (100 ug/ml), 2 ul oNTP mix (10 mM each ATP, dCTP, dGTP, dTTP), 1 ul 10 mM spermidine-HCl, 1 ul 80 mM sodium pyrophosphate and 125 units human placental ribonuclease inhibitor (HPRNI). 10 units of avian myloblastoma virus (AMV) reverse transcriptase were added to give a final reaction volume of 20 ul before incubation for 1 hour at 42° C. The reaction was terminated by addition of 20 ul 0.1M NaCl, 40 mM EDTA. The length and quality of the products were assessed by setting up a parallel reaction containing 50 uCi of $^{32}P$-labelled dCTP (3000 Ci/mmol). The labelled reaction products were fractioned through an alkaline gel that was subsequently autoradiographed. The bulk of labelled products fell within the 200 to 2000 bp size range, with larger products clearly visible.

The oligo dT primer was removed by selective precipitation. 0.5 ug poly I. poly C (Pharmacia) and 3 ul 10% (w/v) CTAB were added to the reaction mix before centrifugation in a microcentrifuge at room temperature for 20 minutes. The supernatant was carefully removed and the pellet resuspended in 14 ul 1M NaCl to which 25 ul $H_2O$ and 1 ul 10% CTAB were added and the sample was again pelleted in a microcentrifuge. The pellet was finally resuspended in 10 ul 1M NaCl and precipitated in 2.7 vol ethanol overnight at −20° C. The pellet was washed in 70% ethanol and dissolved in 7 ul $H_2O$. A dG tailing reaction was performed by adding to this sample; 4 ul 5×tailing buffer (1M potassium cacodylate. 125 mM Tris HCl, pH 7.2), 1 ul 2 mM DTT, 2 ul 5 mM cobalt chloride, 5 ul 20M dCTP and 25 units Terminal transferase (Boehringer) and incubating at 37° C. for 20 minutes before terminating with 4 ul 100 mM EDTA and 2 ul 1M NaCl. Excess nucleotides were removed by adding 1 ul 10% (w/v) CTAB and spinning in a microcentrifuge at 4° C. for 20 minutes. The pellet was dissolved in 10 ul 1M NaCl before addition of 0.25 ug glycogen and 30 ul of cold ethanol and reprecipitation overnight at −20° C. After washing tho pellet in 70% ethanol it was dissolved in 20 ul 50 mM NaOH.2 mM EDTA and incubated at 65° C. for 60 minutes to hydrolyse the RNA. The cDNA was again ethanol precipitated, washed and the pellet dissolved in 20 ul $H_2O$.

7.2 PCR Amplification 7.2 PCR amplification of homopolymer tailed first strand cDNA utilized the amplimers;

A (oligo $dT_{17}$-Not I); GCGGC-CGCTTTTTTTTTTTTTTTT

B (oligo $dC_{14}$-Eco RI); AAGGAATTC-CCCCCCCCCCCC

The PCR reactions contained 10 ul 10×PCR buffer (100 mM Tris HCl, pH 8.3, 500 mM KCl, 40 mM $MgCl_2$, 0.1% gelatin), 10 ul 10×dNTP mix (5 mM dATP, dCTP, dGTP, dTTP). 100 pmoles amplimer A, 100 pmoles amplimer B, 2 units Taq polymerase and 1–10 ng oligo (dG) tailed cDNA in a total reaction volume of 20 ul overlaid with 20 ul mineral oil. The following thermal cycling regime was then performed; 1 cycle 96° C., 2 minutes to denature the products; (96° C., 2 minutes, 58° C., 2 minutes, 72° C., 3 minutes) to allow second strand synthesis, 1 cycle (96° C., 2 minutes, 40° C., 2 minutes, 72° C. 2 minutes) to ensure good priming from the oligo (dT) end: 15 cycles (96° C. 2 min; 58° C. 2 min; 72° C. 3 min) to amplify the products. The reaction mix was fractionated by electrophoresis through a NuSieve GTG LMP (FMC Bioproducts) gel using 123 bp DNA ladder as size marker and regions of the gel corresponding to size classes of <500.500 to 1500, 1500 to 2000 and >2000 bp were excised and recovered from the gel by freezing at −20° C. then centrifuging in a microfuge for 10 min in Spin-X filters (Costar). The PCR products were Southern blotted and hybridized to 3 clones known to be constitutively expressed in potato roots. cDNA probes of long and short and high and low abundance transcripts hybridized to PCR products reflecting a fair representation of different transcripts with the library.

7.3 Library Construction

The recovered DNA (greater than 200 bp) was digested with EcoRI and NotI and ligated into similarly digested lambda-ZAP before packaging in vitro using Stratagene Giga Plus packaging min according to the manufacturers instructions. The library was titred on E. coli strain XL1-Blue using LB plates with 1% top agar containing 12.5 mM IPTG and 6.25 mg/ml X-gal.

7.4 Assessment of library

The quality of the PCR based cDNA library was assessed in two ways, (i) approximately 96% of plaques proved to be recombinants as shown by insertional inactivation of betagalactosidase alpha-complementation. (ii) Plaques picked at random into PCR buffer and amplified using complementary M13 amplimers showed single inserts ranging from 230 bp-1000 bp with an average insert size of 470 bp.

7.5 Differential Screening

The library yielded $3.5 \times 10^5$ recombinant phase of which $6 \times 10^4$ were screened with $^{32}P$ dCTP-labelled probes synthesized as first strand cDNA from 10 ul total RNA prepared from either infected root tissue 26 days post Ro2 invasion or from healthy roots of equivalent age (Curr S J. McPherson H J 1991 *PCR-based cDNA library construction, In: McPherson M J. Quirke P. Taylor G R (eds) Polymerase chain reaction: A practical approach.* IRL Press at Oxford University Press, Oxford). Unincorporated isotope was removed by precipitation with ammonium acetate and the probes adjusted to give equivalent cpm/ug cDNA/ml hybridization fluid following liquid scintillation counting. Plaque lifts were performed in duplicate and were denatured in 0.5M NaOH. 1.5M NaCl and neutralized in 1.5 mNaCl, 0.5M Tris pH7.2 and 1 mM EDTA and baked (80° C., 2 hours). Filters were prehybridized in separate "healthy" and "infected" prehybridization fluid containing 5×SSPE, 6% PEG 6000, 0.5% Marvel (skimmed milk powder) 1% SDS, 0.1% sodium pyrophosphate and 250 ug/ml ultrasonicated and denatured herring sperm DNA at 65° C. for 6 hours. Hybridization was at 65° C. for 24 hours following addition of the appropriate radiolabelled 1st strand probe. Following hybridization the filters were washed sequentially in 5×SSC, 0.1% SDS then 1×SSC, 0.1% SDS at 65° C. for 2×20 min changes in each solution. The blots were exposed to X-ray film, with intensifier screens at −70° C. Plaques which hybridized to Ro2 day 26 probe and not to healthy day 26 probe were purified to homogeneity by 2 further rounds of plaque screening.

8. Northern and Southern hybridization and probe preparation

RNA loaded at 10 ug per track was separated through 0.6M formaldehyde agarose gels running at 7.5 Vcm$^{-1}$. The gel was photographed and rinsed 2×20 min in 10×SSC and blotted onto Hybond-N membrane (Amersham) with 10×SSC. Filters were baked (80° C., 2 hr) and prehybridized for 12 hours at 42° C. in 50% formamide, 5×SSC, 1×Denhardts, 100 ug/ml herring sperm DNA and 250 mM phosphate buffer, (pH 6.5). Hybridization was performed in fresh prehybridization buffer including heat denatured $^{32}P$-hexaprime-labelled pPSR 2–4 probe (25 ng) (Feinberg, A P & Vogelstein, B 1983 *Nucleic Acids Research* 14, 2229) at 42° C. for 24 hours. The filters were washed sequentially in 5×SSC 0.1% SDS at 42° C. then 2×SSC 0.1% SDS at 42° C. with a final wash at 65° C. in 2×SSC 0.1% SDS. The blots were exposed to X-ray film, with intensifier screens, at −70° C. PMR1 insert was prepared by picking a single purified plaque into PCR buffer and amplifying with complementary M13 amplimers according to Gussow, D & Clackson, T (1989 *Nucleic Acids Research* 17, 4000).

Genomic DNA was prepared from nuclei isolated from young potato leaves (cultivar Maris Piper) as described by Jofuku, K D & Goldberg, R B (1989, *In Plant Molecular Biology: A Practical Approach* (ed C S Shaw) pp 37–66). The high molecular weight DNA was size fractionated through a 0.6% agarose gel following digestion with the restriction enzymes. To analyse gene expression throughout the plant, RNA was extracted from stems, peticles, leaves, flowers and roots from both infected and uninfected plants. To analyse the wound response, plant roots or leaves were crushed and RNA extracted from treated tissue over a time-course (3, 6, 9 and 12 hours post crushing). Samples were compared by Northern analysis with RNA extracted from nematode infected roots. Gels were depurinated, denatured and blotted onto Hybond-N membrane (Sambrook, J. Fritsch, E F & Maniatis, T (1989 *Molecular Cloning: A laboratory manual* 2nd edn. Cold Spring Harbour Press). The filter was baked (80° C., 2 hr) and prehybridized for 6 hours at 65° C. in prehybridization fluid as described for differential screening of plaques. Homogenous hybridization and washing conditions wore as described for northern blot filters. Heterologous hybridizations were performed at 56° C. and fillers were washed in 5×SSC at 56° C.

9. Excision of pBluescript from lambda ZAP and plasmid purification pBluescript clone PMR1, carrying the insert whose sequence is shown in one of formulae 1 to 8, was excised from a positively hybridizing lambda ZAP clone and rescued according to the instructions in the Stratagene manual. Plasmid DNA was purified by caesium chloride density gradient centrifugation (Davis L. G. Dibner H D. Batey J F 1986 *Basic methods in molecular biology* Elsevier Science Publishers, N.Y.)

10. Sequence analysis

DNA sequence analysis was performed on alkaline denatured plasmid DNA according to the methods described in the manufacturers protocols for Sequenase (Version 2.0) reactions (United States Biochemical Corp). DNA sequence data were compared with the EMBL data base and GenBank database (release 25) by using the QUICKN program that uses the algorithm of Lipman and Pearson (Lipman D J K, Pearson V R 1985 *Rapid and sensitive protein similarity searches* Science 227: 1435–1441) running an a VAX 11/750 computer VMS operating system.

11. Isolation of genomic clone

A lambda EMBL3 genomic DNA library was constructed using partial EcoRI digested cv Maris Piper genomic DNA according to methods described by Sambrook et al (1989) ibid. The library was screened by plating approx $1.8 \times 10^5$ clones, preparing duplicate plaque lift filters, prehybridising then hybridising and washing essentially as previously described under Section 7.5 except that the probe was prepared by hexa-prime labelling insert DNA. PCR amplified (Gussow D, Clackson T 1989 *Direct clone characterization from plaques and colonies by the polymerase chain reaction* Nucleic Acids Res 17:10) from the cDNA clones, pPMR1, pPMR2 or pPMR3.

Positively hybrising clones recovered after 3 rounds of hybridisation screening were further characterised by restriction analysis and DNA sequencing Sambrook et al (1989 ibid) to localise promoter sequences.

12. In situ hybridisations

Tissue from infected and uninfected roots were embedded in wax, sectioned, prehybridised then hybridized to sense and antisense probes of pPMR1, pPMR2 and pPMR3 as described by Jackson D. (*In Molecular Plant Pathology: A Practical Approach* (ed. S J Gurr, H J McPherson and D J Bowles IRL Press, Oxford, 1991).

13. Production and regeneration of transgenic plants

Transgenic potatoes were produced according to the methods described by Horsch et al (1985 *Science* 227, 1229–1231) using the Agrobacterium strain GV3101 containing pGV3850, carrying feeding call specific promoters fused to an appropriate disruptive gene selected from those mentioned in the Introduction to this specification, and plantlets were regenerated prior to testing for nematode resistance.

EXAMPLE 2

Presence of equivalent genes in other plant species

Genes from one species of plant can be expressed in a temporally and spatially correct manner in a second species even when the species belong to different plant families. Due to the similarity in physiology and pathology of syncytium establishment and life cycles of cyst nematodes on a range of plants from many families, a gene expressed within the syncytium of one plant will be correctly expressed upon introduction to a different plant species.

Confirmation is obtained by identifying equivalent genes within other species of plants. Tobacco, tomato and sugar beet genomic DNA digests were examined by hybridization to pPMR1 (following the method of Section 8). In all cases cross hybridization was observed showing that equivalent genes exist In these plants. A construct comprising the promoter of the gene represented by pPMR1 is therefore capable of directing the correct localised expression of a suitable anti-nematode gone in a range of crop plants. These experiments also provide a route to the isolation of the equivalent genes from other species of plant for the expression of an anti nematode defence mechanism therein.

We claim:

1. A method of controlling nematodes, the method comprising the steps of:
    a) identifying a gene, the promoter region of said gene being specifically induced within a successfully nematode infected plant by nematode infection of the plant;
    b) preparing a construct by combining said promoter region of said gene with a further region, wherein said further region codes for a product disruptive of nematode attack; and
    c) transforming plants with said construct to obtain plants which are thus nematode resistant.

2. A method according to claim 1, wherein said identification is of a gene induced at a nematode feeding site.

3. A method of controlling nematodes as claimed in claim 1, comprising the steps of constructing a cDNA library by use of a polymerase chain reaction (PCR); comparing said library with cDNA of infected and uninfected plants; and identifying a cDNA clone representing a gene expressed at the feeding site and using the cDNA clone to isolate a corresponding genomic clone.

4. A method of controlling nematodes as claimed in claim 2, comprising the steps of constructing a cDNA library by use of a polymerase chain reaction (PCR); comparing said library with cDNA of infected and uninfected plants; and identifying a cDNA clone representing a gene expressed at the feeding site and using the cDNA clone to isolate a corresponding genomic clone.

5. A method according to claim 1, wherein the promoter region of said gene is combined with a coding region, which coding region codes for a product disruptive of nematode attack.

6. A method according to claim 2, wherein the promoter region of said gene is combined with a coding region, which coding region codes for a product disruptive of nematode attack.

7. A method according to claim 3, wherein the promoter region of said gene is combined with a coding region, which coding region codes for a product disruptive of nematode attack.

8. A method according to claim 4, wherein the promoter region of said gene is combined with a coding region, which coding region codes for a product disruptive of nematode attack.

9. A method according to claim 5, wherein said coding region is a region coding for means adapted to kill a cell which attempts redifferentiation towards feeding site development.

10. A method according to claim 9, wherein said means is selected from the group consisting of:
    i) DNAase, RNAase or proteinase, toxic protein or toxic peptide;
    ii) a multi-gene toxic syndrome; and
    iii) antisense RNA to the redifferentiated cells.

11. A method according to claim 5, wherein said coding region is a region coding for a product having a lethal or pronounced sub-lethal effect on ingestion by a nematode.

12. A method according to claim 11, wherein said product is selected from the group consisting of:
    i) a nematode toxic protein;
    ii) an antibody disruptive of nematode feeding; and
    iii) a nematode toxic neuropeptide.

13. A method of controlling nematodes according to claim 1, wherein the nematodes are root cyst nematodes.

14. A method of controlling nematodes according to claim 1, wherein the plant to which nematode resistance is conferred is potato, tomato, soybean, sugar beet, oilseed rape, wheat, oats, barley, rice, carrot, brassicas or tobacco.

15. A nematode resistant transgenic plant incorporating a modified gene derived from a method according to claim 1.

16. A nematode resistance gene comprising a promoter of a gene induced by nematode infection of a plant, and a coding region, which coding region codes for a product disruptive of nematode attack.

* * * * *